United States Patent [19]

Hazen et al.

[11] Patent Number: 5,011,997
[45] Date of Patent: Apr. 30, 1991

[54] PROCESS FOR BIS(4-AMINOPHENYL)HEXAFLUOROPROPANE

[75] Inventors: James R. Hazen, Coventry; William R. Lee, E. Providence, both of R.I.

[73] Assignee: Hoechst Celanese Corp., Somerville, N.J.

[21] Appl. No.: 105,857

[22] Filed: Oct. 7, 1987

[51] Int. Cl.$^5$ .................. C07C 211/50; C07C 209/50
[52] U.S. Cl. .................................... 564/335; 564/330; 564/414
[58] Field of Search ............... 564/330, 158, 335, 181, 564/414

[56] References Cited

U.S. PATENT DOCUMENTS

| | | | |
|---|---|---|---|
| 902,150 | 10/1908 | Heidenreich | 564/414 X |
| 1,850,526 | 3/1932 | Zitscher | 564/414 X |
| 2,334,201 | 11/1943 | Kamm et al. | 564/414 X |
| 2,822,396 | 2/1958 | Dent | 564/414 X |
| 3,897,498 | 7/1975 | Zengel et al. | 564/414 |
| 3,904,691 | 9/1975 | Carnmalm et al. | 564/414 X |
| 4,082,749 | 4/1978 | Quadbeck-Seeger et al. | 564/414 X |
| 4,198,348 | 4/1980 | Bertini et al. | 564/414 |

OTHER PUBLICATIONS

Houben-Weyl, "Stickstoff Verbindungen", Methoden der Organischen Chemie, vol. 10, Part 3, pp. 375–377 (1965).

Primary Examiner—Glennon H. Hollrah
Attorney, Agent, or Firm—Perman & Green

[57] ABSTRACT

This invention is an improved process for preparing 2,2-bis(4-aminophenyl)hexafluoropropane which comprises subjecting 2,2-bis(4-aminocarbonylphenyl)hexafluoropropane to the Hofmann reaction and then treating that reaction product under reducing conditions to produce the desired amine in high yield.

7 Claims, No Drawings

PROCESS FOR BIS(4-AMINOPHENYL)HEXAFLUOROPROPANE

BACKGROUND OF THE INVENTION

The aromatic diamine 2,2-bis(4-aminophenyl)hexafluoropropane is a known product which is useful in the preparation of polyimides and polyamides These polymers are known in the literature; see e.g. U.S. Pat. No. 3,356,648 and U.S. Pat. No. 3,328,352. These polymers possess high thermal stability, enhanced light transparency, and improved processing characteristics. These properties give such polymers application in areas where high service temperature stability is required, such as aircraft composites and high temperature shaped parts and films. They are prepared by reacting the aromatic diamine with a dianhydride or dicarboxylic acid chloride to produce the polyimide or polyamide, respectively The literature describes several methods to prepare the 2,2-bis(4-aminophenyl)hexafluoropropane intermediate. U.S. Pat. No. 3,328,352 teaches its preparation by the direct condensation of aniline with hexafluoroacetone in the presence of an aluminum chloride catalyst The reaction conditions are severe and the reported yield is very low—approximately 26 percent.

Another literature preparation is reported in Chemical Abstracts, 65, 185236. This method involves the application of the Curtius rearrangement of the diacyl azide prepared from the corresponding dicarboxylic acid chloride; i.e., 2,2-bis(4-chlorocarbonylphenyl)hexafluoropropane. However, here again the reported yield is low—only 42 percent.

Another literature preparation is reported in U.S. Pat. No. 3,310,573. This method involves the application of the Schmidt reaction [R. F. Schmidt, Ber., 57, 704 (1924)] on the 2,2-bis(4-carboxylphenyl)hexafluoropropane. Here, the dicarboxylic acid is reacted with hydrazoic acid to give the desired diamine directly. The yield again is reported "poor" with no specific value reported.

The low yields of the above literature reports apparently prompted another approach to produce the desired diamine. Lau et al [J. Polymer Science, Polymer Chemistry Edition, 20, 2381 (1982)] reported its preparation from 2,2-bis(4-hydroxyphenyl)hexafluoropropane. Here, the commercially available dihydroxy compound was reacted with 2-chloro-4-phenylquinazoline to give the bis quinazoline condensation product which was then thermally rearranged to the quinazolinone which was then hydrolzyed to the diamine. Again, the reported yield was low—just 16.5 percent. In addition the method requires severe reaction conditions and a chromatographic purification of the product which is not readily adapted to a commercial manufacturing process.

It is the object of this invention to produce high purity 2,2-bis(4-aminophenyl)hexafluoropropane in high yield from readily available materials by a simple, commercially feasible process.

SUMMARY OF THE INVENTION

This invention is that of an improved process for the preparation of 2,2-bis(4-aminophenyl)hexafluoropropane in vastly improved yield over the prior art by a practical, commercially feasible method.

The process comprises reacting the 2,2-bis(4-aminocarbonyl)hexafluoropropane with alkali hypohalite and then subjecting the reaction product to reducing conditions to produce the desired diamine in an overall yield of 90 percent or greater. The first step of the process is known in the literature as the Hofmann Reaction for the conversion of an amide to the primary amine but it does not produce a high purity product in high yield but rather a low purity reaction product which is extremely difficult to purify The second process step comprises subjecting the Hofmann reaction product to reducing conditions which converts the by-products of the Hofmann reaction to the desired diamine.

DESCRIPTION OF THE PREFERRED EMBODIMENTS

The process of the invention comprises the following reaction scheme:

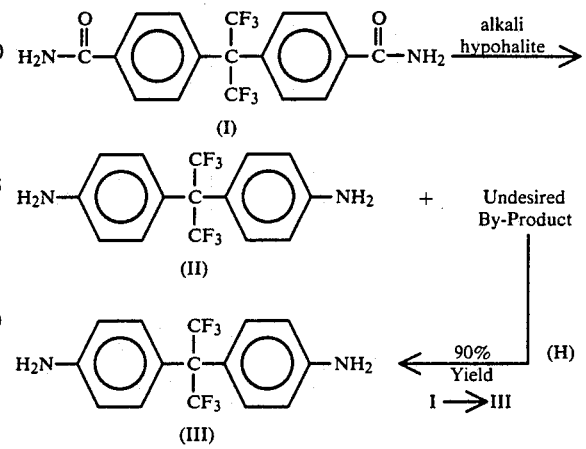

Although the above reaction scheme is presented in terms of the unsubstituted diamine, it may be a substituted or unsubstituted aromatic diamine having the following generic formula:

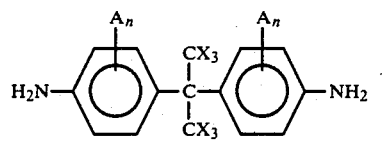

wherein: A is a substituent which is independently selected from lower alkyl of 1 to 3 carbons, chloro or fluoro; n is an integer independently selected from 0 to 2; and X is a halogen selected from chloro and fluoro.

The process of the invention comprises a first step (I) of subjecting the starting amide to the Hofmann Reaction. The amide is prepared from the known dicarboxylic acid or its acid chloride by conventional techniques; for instance, by reacting the dicarboxylic acid in the presence of ammonia and thermally converting the salt to the amide or forming the acid chloride by reacting the dicarboxylic acid with thionyl chloride, phosphorus trichloride or phosphorous pentachloride, preferably thionyl chloride, and then treating the acid chloride with ammonia; see also March, J., Advanced Organic Chemistry: Reactions, Mechanisms and Structure, 3rd Edition, pages 370–379, John Wiley & Sons, NY (1985).

Step (I) of the process is known as the Hofmann Reaction and it has been extensively reviewed in the literature; see e.g. Wallace, E. S. and Lane, J. S.; Organic Reactions; Vol. 3, p. 267-306, John Wiley & Sons (1964); Smith, P. A. S. in Molecular Rearrangements, Editor DeMao, P. Chapter 8, Interscience Publishers, NY (1967)1; and A. W. Hofmann, Ber., 14, 2725 (1881)—the teachings of which are hereby incorporated by reference.

The Hofmann Reaction comprises the treatment of an amide with a hypohalite such as sodium hypobromite or sodium hypochlorite in the presence of an alkali metal hydroxide; preferably sodium hypochlorite is used as it is readily available. Alternately, the hypohalite may be formed in situ from the halogen (chlorine or bromine) in the presence of sodium hydroxide.

In the presence of the hypohalite, the amide is converted to the amine in the Hofmann Reaction. However, in the case of 2,2-bis(4-aminocarbonyl)hexafluoropropane, the reaction produces a mixed reaction product comprising the desired diamine and a highly colored by-product which can only be removed by a tedious purification process. This by-product was produced in an amount of about 20-40 percent by weight. The purification process involved multiple acid extractions and recrystallizations which in turn reduced the yield even further The color and amount of the by-products was not anticipated nor is it reported in the literature and attempts to eliminate or prevent its formation by modification of the reaction parameters were unsuccessful.

It was discovered that the by-product was a previously unknown or at least unreported dimeric azo compound having the structure:

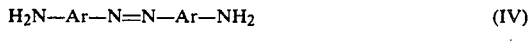

$$H_2N-Ar-N=N-Ar-NH_2 \quad (IV)$$

wherein
Ar is:

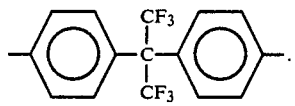

It was thought that this azo by-product could be converted to the desired 2,2-bis(4-aminophenyl)propane by subjecting the reaction product to reducing conditions, under which the azo group is reduced by the sequential addition of hydrogen atoms across the nitrogen to nitrogen double bond to form the hydrazo compound, followed by further reduction, i.e., the addition of hydrogen atoms to the hydrazo compound, to cleave the nitrogen to nitrogen single bond and form the desired diamine. Various methods are known to convert azo compounds to amines, all of which involve a reduction reaction; see generally, Newbold, B. T., in The Chemistry of the Hydrazo, Azo, and Azoxy Groups, Editor Patai, S., Part II, Chapter 15, John Wiley & Sons, NY (1975). This reference discloses a variety of reduction reactions. Preferably, the reduction is conducted by catalytic hydrogenation; see, Freifelder, M., Practical Catalytic Hydrogenation, Chapter 11, Wiley-Interscience, NY (1971). The above references are hereby incorporated by reference.

It was found that the azo by-product was preferably converted to the desired diamine (III) by hydrogenation of the reaction product in the presence of nickel or a noble metal catalyst such as palladium, platinum or rhodium; palladium on a carbon carrier was found to be effective.

The overall yield of the process of the invention has been found to be in excess of 90 percent of theoretical based upon the starting diamide. Also, the technically pure reaction product can be easily purified by conventional techniques to high purity suitable for polymer synthesis, which is another advantage of the process of the invention. This high purity could not be obtained from the crude reaction mixture of the Hofmann reaction by standard purification techniques.

In summary, the process of the invention can be conducted by slurrying the 2,2-bis(4-aminocarbonylphenyl)hexafluoropropane in an excess of aqueous alkali, preferably sodium hydroxide, and treating it with a slight equivalent excess of alkali metal hypohalite (i.e. about 2.2 moles of hypohalite per mole of diamide; preferably sodium hypochlorite at about $-5°$ C. to about 10° C., preferably about 0° C. After several hours, the homogeneous reaction mixture is gradually allowed to warm to room temperature and then the reaction is finished by warming it to 30°-50° C., preferably about 35°-40° C. for 10-60 minutes.

It was determined that a preferable effective amount of hypohalite reactant was about 10 to 15% molar excess—the theoretical amount being 2 moles of hypohalite per mole of diamide. Higher excesses of the hypohalite are effective to convert the diamide to diamine but that will increase the amount of azo compound formation, which increases the severity of the reaction conditions in the second step of the process—the reduction step. Lower amounts of the hypohalite, of course, requires more severe reaction conditions in the initial step—the Hofman Reaction, or results in incomplete reaction. It will be apparent to the skilled worker in the field to determine the effective amount of hypohalite that person wishes to employ in the Hofmann Reaction to convert the diamide to diamine; e.g. any amount may be used from theoretical to a large excess.

The reaction product is then subjected to reducing reaction conditions to convert the by-product (IV) to the desired diamine (III). The reduction is preferably conducted over a palladium-on-carbon catalyst in a hydrogen atmosphere. The hydrogenation may be conducted on the direct reaction product of the first step (the Hofmann Reaction product) or the isolated crude reaction product. Preferably, the reduction is conducted on the isolated crude reaction product in any suitable hydrogenation solvent such as a lower aliphatic alcohol.

The following Example illustrates this invention.

EXAMPLE 1

Into 250 parts of water is added 67.5 parts of 50% sodium hydroxide which cooled to 0°-5° C. and 30 parts of 4,4'-[2,2,2-trifluoro-1-(trifluoromethyl)ethylidene]-bis-benzamide, or 2,2-bis (4-aminocarbonylphenyl)hexafluoropropane is added. The mixture is stirred until a uniform slurry forms. Then 105 parts of 12% sodium hypochlorite solution is added at 0°-5° C. over 30-45 minutes. After about four hours at 0°-5° C., the reaction mixture is allowed to warm to room temperature and then warmed to 35°-40° C. for 30-45 minutes. The mixture is cooled to 25° C. or less and treated with about 45 parts of acetic acid to pH 7.5. After stirring 15 minutes at pH 7.5, the slurry is filtered and washed thoroughly with water. The moist product mixture, containing about 80-85% of 2,2-bis(4-aminophenyl)hexafluoropropane and about 15-20% of azo product IV, is vacuum filtered to remove excess water. The crude yield is 25.5 parts (dry weight).

The moist crude product is charged into 100 parts by volume of methanol and hydrogenated in an autoclave over 1.0 part of 3% palladium-on-carbon at 350 psig $H_2$ at 110°–120° C. After several hours, the catalyst is filtered off and the product isolated by drowning into 700 parts by volume of water and ice. The slurry is filtered and washed with water. The product is isolated in an overall yield of 91% of theory based on starting diamide and has an assay of about 95% and m.p. 190°–193° C. The product is further purified by the aqueous reprecipitation from its hydrochloride salt and by reprecipitation of a methanolic solution with distilled water to give the pure diamine, m.p. 195°–198° C.

Although the above invention has been described in terms of the preparation of 2,2-bis(4-aminophenyl)hexafluoropropane many different embodiments of the process of the invention may be made without departing from the scope of the invention. The hydrogen atoms of the phenylene rings of the desired diamine may be substituted with non-interfering substituents without departing from the scope of the invention; for example, the hydrogen atoms may be replaced with lower alkyl of 1 to 3 carbons or halogen substituents such as chloro and bromo. Similarly, one or more of the fluoro substituents of the linking isopropylidene group may be replaced with chloro substituents; e.g. the starting amide reactant could be 2,2-bis(4-aminocarbonylphenyl)dichlorotetrafluoroisopropane [2,2-bis(4-benzamido)dichlorotetrafluoropropane].

The invention has been described by way of the above specification and illustrative examples and it is to be understood that this invention is not limited to the specific embodiments thereof except as defined by the following claims.

I claim:

1. A process for the preparation of a substituted or unsubstituted aromatic diamine having the formula:

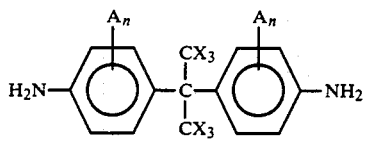

wherein: A is a substituent which is independently selected from lower alkyl of 1 to 3 carbons, chloro or fluoro; n is an integer independently selected from 0 to 2; X is a halogen selected from chloro and fluoro; comprising:

(1) a first step of dispersing in an alkaline reaction medium an aromatic diamide of the formula:

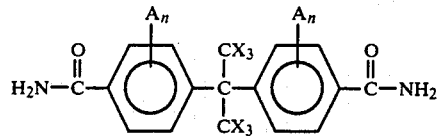

wherein A, n and X have the meanings set forth above;

(2) a second step of contacting said diamide with an alkali metal hypohalite in an amount effective to rearrange said diamide to said diamine; and (3) subjecting said reaction mixture of said second step to reducing conditions whereby any reaction by-product formed in said second step is converted to said diamine.

2. A process according to claim 1 wherein said alkali metal hypohalite is selected from sodium hypochlorite and sodium hypobromite.

3. A process according to claim 1 wherein said reducing conditions comprise hydrogenating said second step reaction mixture in the presence of hydrogen and hydrogenation catalyst.

4. A process according to claim 1 wherein said diamide is 2,2-bis(4-aminocarbonylphenyl)hexafluoropropane.

5. A process according to claim 2 wherein said diamide is 2,2-bis(4-aminocarbonylphenyl)hexafluoropropane.

6. A process according to claim 3 wherein said diamide is 2,2-bis(4-aminocarbonylphenyl)hexafluoropropane.

7. A process according to claim 4 wherein said alkali metal hypohalite is selected from sodium hypochlorite and sodium hypobromite and said reducing conditions comprise hydrogenation of said second step reaction mixture in the presence of hydrogen and a hydrogenation catalyst.

* * * * *